(12) United States Patent
Parri et al.

(10) Patent No.: US 6,217,792 B1
(45) Date of Patent: Apr. 17, 2001

(54) CHIRAL DOPANTS

(75) Inventors: Owain L Parri; Patrick Nolan, both of Poole; Louise D Farrand, Manchester; Alison May, Wimborne, all of (GB)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/214,387

(22) PCT Filed: Jun. 18, 1997

(86) PCT No.: PCT/EP97/03167
§ 371 Date: Dec. 30, 1998
§ 102(e) Date: Dec. 30, 1998

(87) PCT Pub. No.: WO98/00428
PCT Pub. Date: Jan. 8, 1998

(30) Foreign Application Priority Data

Jul. 1, 1996 (EP) .................................. 96110578

(51) Int. Cl.⁷ ............................ C09K 19/34; C09K 19/00
(52) U.S. Cl. ....................... 252/299.61; 428/1.1
(58) Field of Search ........................ 252/299.61; 428/1.1

(56) References Cited

U.S. PATENT DOCUMENTS 5,753,141 * 5/1998 Siemensmeyer et al. ...... 252/299.62

FOREIGN PATENT DOCUMENTS

| 4342280 | 6/1995 | (DE) . |
| 0070401 | 1/1983 | (EP) . |
| 747382 | 12/1996 | (EP) . |

OTHER PUBLICATIONS

Chem. Abs. 111:144537, 1989.*
Indian Journal of chemistry, Sec. B, vol. 16b, No. 2, 1978, pp. 153–55, XP002042395, see compound No. 3.

V. Vill et al.: "Ferroelectrishe Flussigkristall–Mischungen mit Kohlenhydrat–Derivaten als Dotierstoffe" Zeitschrift Fur Naturfoschung A, Journal of Physical Science, vol. 44a, No. 7, 1989, pp. 675–679, XP002042393, see whole document.

V. Vill et al.: "Molekulares Verdrillungsvermogen von Kohlenhydrat–Derivaten" Zeitschrift Fur Naturfoschung A., Journal of Physical Science, vol. 43a, No. 12, 1988, pp. 1119–1125, XP002042394, see whole document.

* cited by examiner

Primary Examiner—C. H. Kelly
(74) Attorney, Agent, or Firm—Millen White Zelano & Branigan

(57) ABSTRACT

The invention relates to chiral dopants of the formula (I): $R^1—X^1—MG^1—G—MG^2—X^2—R^2$. The invention also relates to liquid crystalline materials comprising at least one chiral dopant of formula (I) and optionally at least one polymerizable mesogenic compound. The invention furthermore relates to the use of such liquid crystalline materials for the preparation of polymer films with a chiral liquid crystalline phase, for active and passive optical elements or color filters and for liquid crystal displays, for example STN, TN, AMD-TN, temperature compensation, guest-host or phase change displays, or polymer free or polymer stabilized cholesteric texture (PFCT, PSCT) displays. The invention also relates to cholesteric liquid crystal displays comprising liquid crystalline materials comprising chiral dopants of formula (I) and to polymer films with a chiral liquid crystalline phase obtainable by (co)polymerizing a liquid crystalline material comprising at least one chiral of formula (I) and at least one polymerizable compound.

24 Claims, No Drawings

CHIRAL DOPANTS

The invention relates to chiral dopants of formula I

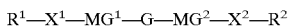

wherein

R¹ and R² are independently of each other a straight-chain or branched alkyl radical with up to 25 C atoms which may be unsubstituted, mono- or polysubstituted by halogen or CN, it being also possible for one or more non-adjacent CH₂ groups to be replaced, in each case independently from one another, by —O—, —S—, —NH—, —N(CH₃)—, —CO—, —COO—, —OCO—, —OCO—O—, —S—CO—, —CO—S— or —C≡C— in such a manner that oxygen atoms are not linked directly to one another, X¹ and X² are independently of each other —O—, —S—, —CO—, —COO—, —OCO—, —OCO—O—, —S—CO—, —CO—S— or a single bond, G is the following chiral bivalent structure element

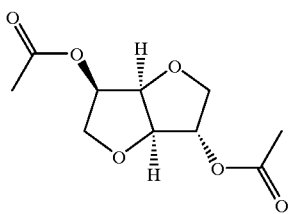

and

MG¹ and MG² are each independently a mesogenic or mesogenity supporting group of formula II

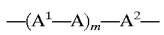     II with

Z denoting —COO—, —OCO—, —CH₂CH₂—, —OCH₂—, —CH₂O—, —CH=CH—, —CH=CH—COO—, —OCO—CH=CH—, —C≡C— or a single bond, A¹ and A² being each independently 1,4-phenylene in which, in addition, one or more CH groups may be replaced by N, 1,4-cyclohexylene in which, in addition, one or two non-adjacent CH₂ groups may be replaced by O and/or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydronaphthalene-2,6-diyl, it being possible for all these groups to be unsubstituted, mono- or polysubstituted with halogen, cyano or nitro groups or alkyl, alkoxy or alkanoyl groups having 1 to 7 C atoms wherein one or more H atoms may be substituted by F or Cl, and m being 0, 1, 2 or 3.

The invention also relates to a liquid crystalline material comprising at least one chiral dopant of formula I and optionally at least one polymerizable mesogenic compound.

The invention furthermore relates to the use of such a liquid crystalline material for the preparation of polymer films with a chiral liquid crystalline phase, for active and passive optical elements or colour filters and for liquid crystal displays, for example STN, TN, AMD-TN, temperature compensation, guest-host or phase change displays, or polymer free or polymer stabilized cholesteric texture (PFCT, PSCT) displays.

The invention also relates to liquid crystal displays comprising a liquid crystalline material comprising at least one chiral dopant of formula I and to polymer films with a chiral liquid crystalline phase obtainable by (co)polymerizing a liquid crystalline material comprising at least one chiral dopant of formula I and at least one polymerizable mesogenic compound.

Chiral dopants are used to induce or enhance a helical twist of the molecules of a liquid crystalline medium that can be used for example in liquid crystal displays. The pitch p of the molecular helix in the first approximation, which is sufficient for most practical applications, is inverse proportional to the concentration c of the chiral dopant in the liquid crystal host mixture according to equation (1):

$$p = \frac{1}{HTP} \cdot \frac{1}{c} \quad (1)$$

The proportionality factor is the helical twisting power (HTP) of the chiral dopant.

For many applications it is desirable to have LC mixtures that exhibit a twist. Among these are e.g. phase-change displays, guest-host displays, passive and active matrix TN and STN displays like AMD-TN, including such displays with temperature compensated characteristics, e.g. by appropriate selection of the cholesteric dopants according to the invention either alone or in combination with further chiral dopants. For these applications it is advantageous to have available a chiral dopant with a high HTP in order to reduce the amount of dopant needed to induce the desired pitch.

For some applications it is desired to have LC mixtures that exhibit a strong helical twist and thereby a short pitch length. For example in liquid crystalline mixtures that are used in selectively reflecting cholesteric displays, the pitch has to be selected such that the maximum of the wavelength reflected by the cholesteric helix is in the range of visible light. Another possible application are polymer films with a chiral liquid crystalline phase for optical elements, such as cholesteric broadband polarizers or chiral liquid crystalline retardation films.

As can be seen from equation (1), a short pitch can be achieved by using high amounts of dopant or by using a dopant with a high HTP.

However, the chiral dopants of prior art often exhibit low values of the HTP, so that high amounts of dopant are needed. This is a disadvantage because, as chiral dopants can be used only as pure enantiomers, they are expensive and difficult to synthesize.

Further and in many cases even more important, when using chiral dopants of prior art in high amounts, they often negatively affect the properties of the liquid crystalline host mixture, such as e.g. the dielectric anisotropy Δε, the viscosity, the driving voltage or the switching times.

There is thus a considerable demand for chiral dopants with a high HTP which are easy to synthesize, which can be used in low amounts, show improved temperature stability of the cholesteric pitch e.g. for utilizing a constant reflection wavelength and do not affect the properties of the liquid crystalline host mixture.

The invention has the object of providing chiral dopants having these properties, but which do not have the disadvantages of the dopants of the state of the art as discussed above.

It has been found that this object can be achieved by the provision of chiral dopants according to formula I.

The inventive chiral dopants contain a chiral structure element based on 1,4:3,6-Dianhydro-D-sorbitol, which is economically and easily available from sugars as natural source.

Chiral polymerizable mesogenic compounds comprising 1,4:3,6-Dianhydro-D-sorbitol as structure element are disclosed in WO 95/16007.

G. Wulff et al. in Makromolekulare Chemie, 188 (4), 731–40 (1987) describe non-mesogenic 1,4:3,6-Dianhydro-D-sorbitol-2,5-dimethacrylate used as chiral crosslinking agent for template-imprinted vinyl and acrylic polymers.

However the compounds described in WO 95/16007 and by G. Wulff et al. are reactive and consequently not sufficiently stable for most applications.

Thus the object of this invention are chiral dopants of formula I

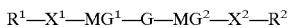

R$^1$—X$^1$—MG$^1$—G—MG$^2$—X$^2$—R$^2$    I wherein

R$^1$ and R$^2$ are each independently a straight-chain or branched alkyl radical with up to 25 C atoms which may be unsubstituted, mono- or polysubstituted by halogen or CN, it being also possible for one or more non-adjacent CH$_2$ groups to be replaced, in each case independently from one another, by —O—, —S—, —NH—, —N(CH$_3$)—, —CO—, —COO—, —OCO—, —OCO—O—, —S—CO—, —CO—S— or —C≡C— in such a manner that oxygen atoms are not linked directly to one another, X$^1$ and X$^2$ are independently of each other —O—, —S—, —CO—, —COO—, —OCO—, —OCO—O—, —S—CO—, —CO—S— or a single bond, G is the following chiral bivalent structure element

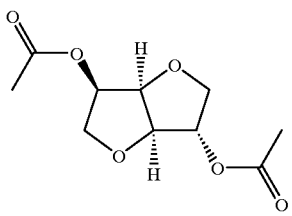

MG$^1$ and MG$^2$ are each independently a mesogenic or mesogenity supporting group of the formula II —(A$^1$—Z)$_m$—Z$^2$—    II with Z denoting —COO—, —OCO—, —CH$_2$CH$_2$—, —OCH$_2$—, —CH$_2$O—, —CH=CH—, —CH=CH—COO—, —OCO—CH=CH—, —C≡C— or a single bond, A$^1$ and A$^2$ being each independently 1,4-phenylene in which, in addition, one or more CH groups may be replaced by N, 1,4-cyclohexylene in which, in addition, one or two non-adjacent CH$_2$ groups may be replaced by O and/or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydronaphthalene-2,6-diyl, it being possible for all these groups to be unsubstituted, mono- or polysubstituted with halogen, cyano or nitro groups or alkyl, alkoxy or alkanoyl groups having 1 to 7 C atoms wherein one or more H atoms may be substituted by F or Cl, and m being 0, 1, 2 or 3.

Another object of the invention is a liquid crystalline material comprising at least one chiral dopant of formula I and optionally at least one polymerizable mesogenic compound.

A further object of the invention is the use of a liquid crystalline material as described above for the preparation of polymer films with a chiral liquid crystalline phase, for active and passive optical elements, colour filters and for liquid crystal displays, for example STN, TN, AMD-TN, temperature compensation, guest-host or phase change displays, or polymer free or polymer stabilized texture (PFCT, PSCT) cholesteric displays.

Another object of the invention are cholesteric liquid crystal displays comprising a liquid crystalline material comprising at least one chiral dopant of formula I.

Yet another object of the invention are polymer films with a chiral liquid crystalline phase obtainable by (co)polymerizing a liquid crystalline material comprising at least one chiral dopant of formula I and at least one polymerizable mesogenic compound.

Of the chiral dopants of formula I particularly preferred are those wherein MG$^1$ and MG$^2$ are selected according to the following formulae:

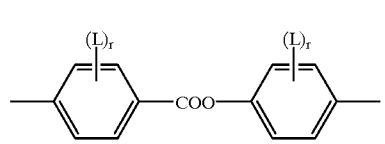

II a

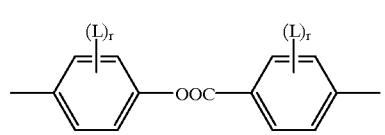

II b

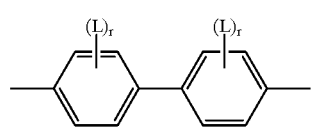

II c

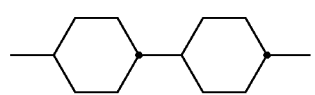

II d

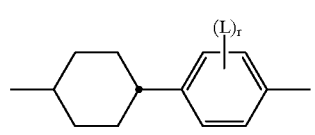

II e

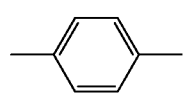

II f

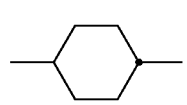

II g

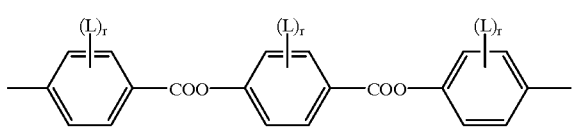

II h

-continued

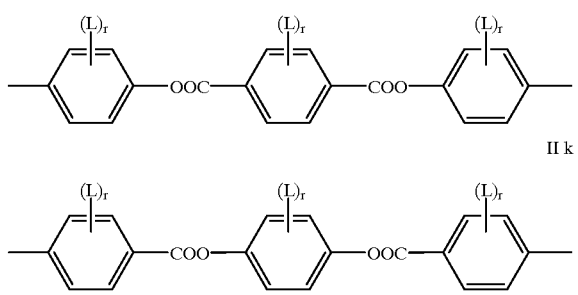

II i

II k

In the formulae II a to II k L denotes, in each case, independently from each other, halogen, a cyano or nitro group or an alkyl, alkoxy or alkanoyl group having 1 to 7 C atoms wherein one or more H atoms may be substituted by F or Cl, and r is 0, 1 or 2.

The group

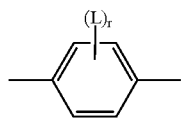

in these preferred formulae is very preferably denoting

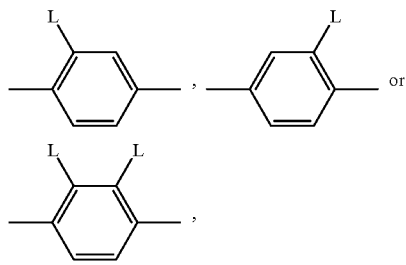

furthermore

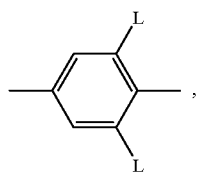

with L having each independently one of the meanings given above.

From the preferred compounds those wherein $MG^1$ and $MG^2$ are selected of formula II a, II b, II c, II d and II e are particularly preferred.

From the preferred compounds especially preferred are those wherein $MG^1$ and $MG^2$ are selected of formula II a and II b.

In these especially preferred compounds r is particularly preferably 0. Furthermore preferred are compounds with $MG^1$ and $MG^2$ being of formula II a and II b wherein at least two aromatic rings are substituted by $(L)_r$ with r being 1 or at least one ring is substituted by $(L)_r$ with r being 2, with L having the meaning given above.

If $R^1$ and/or $R^2$ are an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, methoxy, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2—(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

$R^1$ and $R^2$ in the preferred compounds are preferably alkyl or alkoxy with 1 to 12 C atoms.

$X^1$ and $X^2$ in formula I are preferably denoting —O—, —CO—, —COO—, —OCO— or a single bond.

L is preferably F, Cl, CN, $NO_2$, $CH_3$, $C_2H_5$, $OCH_3$, $OC_2H_5$, $COCH_3$, $COC_2H_5$, $CF_3$, $OCF_3$, $OCHF_2$, $OC_2F_5$, in particular F, Cl, CN, $CH_3$, $C_2H_5$, $OCH_3$, $COCH_3$ and $OCF_3$, most preferably F, $CH_3$, $OCH_3$ and $COCH_3$.

In the compounds of formula I $R^1$ and $R^2$ as well as $MG^1$ and $MG^2$ on both sides of the bivalent chiral group G can be identical or different. Particularly preferred are the compounds of formula I wherein $R^1$ and $R^2$ as well as $MG^1$ and $MG^2$ are identical.

The inventive chiral dopants can be synthesized according to or in analogy to the following reaction schemes:

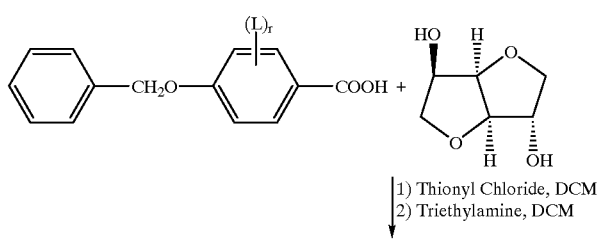

-continued

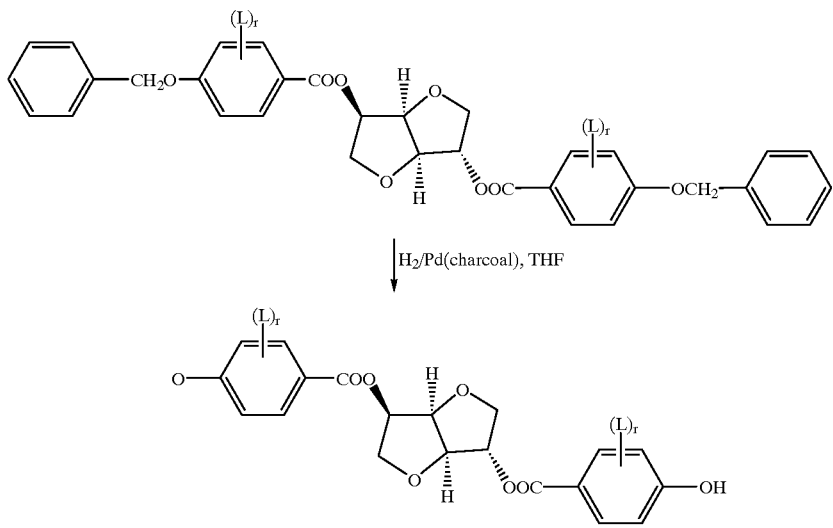

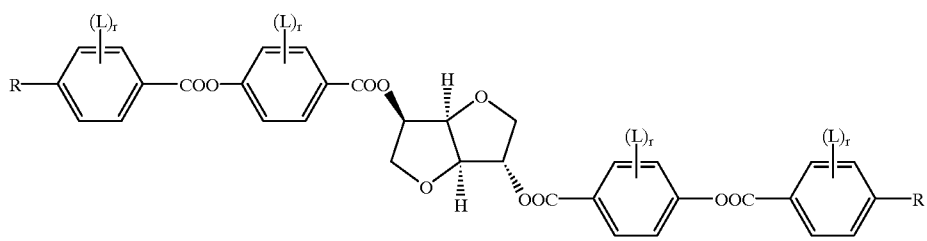

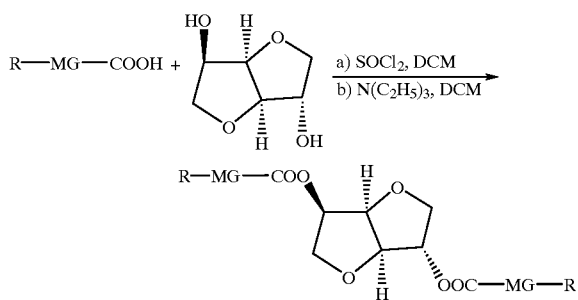

DCCD=dicyclohexylcarbodiimide, DMAP=dimethylaminopyridine, DCM=dichloromethane.

In the reaction schemes 1 and 2 R is denoting an alkyl or alkoxy group with 1 to 12 C atoms, L and r have the meanings given above and MG has one of the meanings of formula II a to II g.

The inventive chiral dopants can be used in liquid crystal materials for displays exhibiting a twisted molecular structure of the liquid crystal matrix like, for example, supertwisted or active matrix liquid crystal displays, or in displays comprising a liquid crystal material with a chiral liquid crystalline phase, like for example chiral smectic or chiral nematic (cholesteric) materials for ferroelectric displays or cholesteric displays.

Thus, another object of the invention is a liquid crystalline material comprising at least one chiral dopant of formula I.

Yet another object of the invention are cholesteric liquid crystal displays comprising cholesteric liquid crystalline materials containing at least one chiral dopant of formula I.

The inventive chiral dopants of formula I exhibit high values of the HTP. Thus liquid crystalline materials with a high helical twist, i.e. a short cholesteric pitch, can be prepared by using the inventive dopants, or otherwise liquid crystalline materials with a medium helical twist can be achieved already when using the inventive dopants in low amounts.

The high HTP values of the inventive dopants makes them also suitable to be used in combination with other dopants for the temperature compensation of the properties of liquid crystal mixtures, such as the cholesteric pitch, and of the properties of displays, e.g. such as the threshold voltage.

In a preferred embodiment of the invention the chiral dopants show a strong temperature dependence of the HTP in nematic liquid crystal mixtures.

The inventive dopants are furthermore advantageous because they are affecting the physical properties of the liquid crystalline material only to a minor extent.

Thus, when admixing the chiral dopants of formula I for example to a liquid crystalline material with positive dielectric anisotropy that is used in a liquid crystal display, $\Delta\epsilon$ is being only slightly reduced and the viscosity of the liquid crystalline material is increased only to a small extent. This leads to lower voltages and improved switching times of the display when compared to a display comprising conventional dopants.

In a particularly preferred embodiment of the invention the chiral dopants show a small temperature dependence of the HTP in nematic liquid crystal mixtures.

The liquid crystalline material according to the invention comprises preferably 0.001 to 15%, in particular 0.01 to 7% and very particularly preferably 0.1 to 4% by weight of chiral dopants of formula I.

The liquid crystalline material according to the invention preferably comprises 1 to 3, very preferably 1 or 2, in particular 1 chiral dopants of formula I.

For temperature compensation applications as described above the liquid crystalline material preferably contains a chiral component which contains at least one chiral dopant of formula I.

In a preferred embodiment of the invention the liquid crystalline material is consisting of 2 to 25, preferably 3 to 15 compounds, at least one of which is a chiral dopant of formula I. The other compounds are preferably low molecular weight liquid crystalline compounds selected from nematic or nematogenic substances, for example from the known classes of the azoxybenzenes, benzylideneanilines, biphenyls, terphenyls, phenyl or cyclohexyl benzoates, phenyl or cyclohexyl esters of cyclohehexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexylpyridazines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl) ethanes, 1-cyclohexyl-2-biphenylethanes, 1-phenyl2-cyclohexylphenylethanes, optionally halogenated stilbenes, benzyl phenyl ether, tolanes, substituted cinnamic acids and further classes of nematic or nematogenic substances. The 1,4-phenylene groups in these compounds may also be laterally mono- or difluorinated.

The liquid crystalline material of this preferred embodiment is based on the achiral compounds of this type.

The most important compounds that are possible as components of these liquid crystalline materials can be characterized by the following formula

wherein L' and E, which may be identical or different, are in each case, independently from one another, a bivalent radical from the group formed by -Phe-, -Cyc-, -Phe-Phe-, -Phe-Cyc-, -Cyc-Cyc-, -Pyr-, -Dio-, -B-Phe- and -B-Cyc- and their mirror images, where Phe is unsubstituted or fluorine-substituted 1,4-phenylene, Cyc is tran-1,4-cyclohexylene or 1,4-cyclohexenylene, Pyr is pyrimidine-2,5-diyl or pyridine-2,5-diyl, Dio is 1,3-dioxane-2,5-diyl abd B is 2-(trans-1,4-cyclohexyl) ethyl, pyrimidine-2,5-diyl, pyridine-2,5-diyl or 1,3-dioxane-2,5-diyl.

G' in these compounds is selected from the following bivalent groups —CH═CH—, —N(ON—, —CH═CY—, —CH═N(O)—, —C≡C—, —CH$_2$—CH$_2$—, —CO—O—, —CH$_2$—O—, —CO—S—, —CH$_2$—S—, —CH═N—, —COO—Phe—COO— or a single bond, with Y being halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is —F, —CF$_3$, —OCF$_3$, —Cl, —NCS or —CN.

In most of these compounds R' and R" are, in each case, independently of each another, alkyl, alkenyl or alkoxy with different chain length, wherein the sum of C atoms in nematic media generally is between 2 and 9, preferably between 2 and 7.

Many of these compounds or mixtures thereof are commercially available. All of these compounds are either known or can be prepared by methods which are known per se, as described in the literature (for example in the standard works such as Houben-Weyl, Methoden der Organischen Chemie [Methods of Organic Chemistry]. Georg-Thieme-Verlag, Stuttgart), to be precise under reaction conditions which are known and suitable for said reactions. Use may also be made here of variants which are known per se, but are not mentioned here.

The inventive dopants are in particular useful for anisotropic polymer gels and for cholesteric liquid crystalline materials for cholesteric displays, such as for example phase change displays or polymer free or polymer stabilized cholesteric texture displays (PFCT, PSCT).

A further advantage of the chiral dopants according to the invention is that cholesteric liquid crystalline materials comprising these dopants exhibit a low temperature dependence of the reflection wavelength dλ/dT (T=temperature, λ=reflection wavelength maximum).

Cholesteric displays are described for example in WO 92/19695, WO 93/23496, U.S. Pat. No. 5,453,863 or U.S. Pat. No. 5,493,430, with the entire disclosure of these documents being introduced into this application by way of reference.

Furthermore, anisotropic polymer gels and displays comprising them are disclosed for example in DE 195 04 224 and GB 2 279 659.

It has been found that PSCT displays comprising the inventive dopants have reduced response times, lower voltages and improved contrast compared to displays comprising conventional dopants, like e.g. R 811 or CB 15, that are commercially available by Merck KGaA (Darmstadt, Germany). For example, a PSCT display in which a conventional dopant was replaced by a chiral dopant according to the invention showed a reduction of the switching time of up to 50%.

A cholesteric film made by using the inventive dopants unexpectedly showed improved brightness, leading to a better contrast between the coloured planar texture and the almost clear focal conic state which is made black using a black backplate.

The inventive chiral dopants and liquid crystal materials comprising these dopants are also particularly useful for the preparation of oriented polymer films with a chiral liquid crystalline phase, such as cholesteric or chiral smetic polymer films.

Examples of oriented cholesteric polymer films used as broad waveband polarizers can be found in EP 0 606 940, whereas I. Heynderickx and D. J. Broer in Mol. Cryst. Liq. Cryst. 203, 113–126 (1991) describe crosslinked cholesteric polymer films that are made of liquid crystalline diacrylates and contain a low molecular weight chiral dopant. EP 0 562 681 A1 discloses polymer networks with a smectic structure that contains chiral low molar mass compounds and exhibits a piezoelectric effect.

It has been found that cholesteric polymer films made by using the inventive chiral dopants are brighter compared to films comprising dopants of prior art like e.g. R 811 or CB 15 as mentioned above.

In order to prepare anisotropic polymer gels or oriented polymer films, the liquid crystalline material in addition to chiral dopants of formula I should also comprise at least one polymerizable mesogenic compound.

Thus, another preferred embodiment of the invention are liquid crystalline materials comprising at least one chiral dopant of formula I and at least one polymerizable mesogenic compound.

The polymerizable mesogenic compounds are preferably selected of formula III $$P—(Sp—X)_n—A—Z^1—B—(Z^2—C)_p—R^3 \quad \text{III}$$

wherein

P is CH$_2$=CW—COO—, WCH=CH—O—,

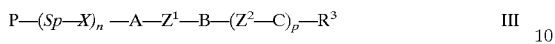

or CH$_2$=CH-Phenyl-(O)$_k$— with W being H, CH$_3$ or Cl and k being 0 or 1,

Sp is a spacer group having 1 to 20 C atoms,

X is a group selected from —O—, —S—, —CO—, —COO—, —OCO—, —OCO—O—, —S—CO—, —CO—S— or a single bond, n is 0 or 1, Z$^1$ and Z$^2$ are each independently —COO—, —OCO—, —CH$_2$CH$_2$—, —OCH$_2$—, —CH$_2$O—, —CH=CH—, —C≡C—, —CH=CH—COO—, —OCO—CH=CH— or a single bond, with halogen, cyano or nitro groups or alkyl, alkoxy or alkanoyl groups having 1 to 7 C atoms wherein one or more H atoms may be substituted by F or Cl, p is 0, 1 or 2, and R$^3$ is an alkyl radical with up to 25 C atoms which may be unsubstituted, mono- or polysubstituted by halogen or CN, it being also possible for one or more non-adjacent CH$_2$ groups to be replaced, in each case independently from one another, by —O—, —S—, —NH—, —N(CH$_3$)—, —CO—, —COO— —OCO—, —OCO—O—, —S—CO—, —CO—S— or —C≡C— in such a manner that oxygen atoms are not linked directly to one another, or alternatively R is halogen, cyano or has independently one of the meanings given for P—(Sp—X)$_n$—.

Polymerizable mesogenic compounds according to formula III are described for example in WO 93/22397; EP 0,261,712; DE 195,04,224; DE 4,408,171 or DE 4,405,316. The compounds disclosed in these documents, however, are to be regarded merely as examples that shall not limit the scope of this invention.

Furthermore, typical examples representing polymerizable mesogenic compounds are shown in the following list of compounds, which should, however, be taken only as illustrative and is in no way intended to restrict, but instead to explain the present invention:

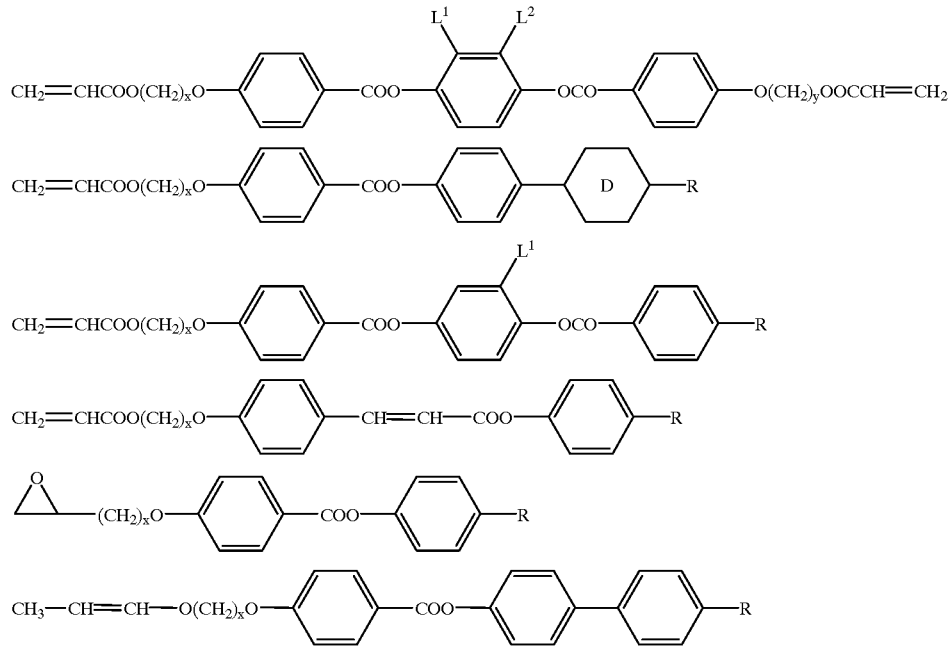

A, B and C are each independently 1,4-phenylene in which, in addition, one or more CH groups may be replaced by N, 1,4-cyclohexylene in which, in addition, one or two non-adjacent CH$_2$ groups may be replaced by O and/or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydronaphthalene-2,6-diyl, it is being possible for all these groups to be unsubstituted, mono- or polysubstituted wherein x and y are each independently 1 to 12, D is a 1,4-phenylene or 1,4-cyclohexylene group, R is halogen, cyano or an alkyl or alkoxy group with 1 to 12 C atoms and L$^1$ and L$^2$ are each independently H, halogen, CN, or an alkyl, alkoxy or alkanoyl group with 1 to 7 C atoms.

The polymerizable mesogenic compounds of formula III can be prepared by methods which are known per se and which are described in the documents cited above and, for example, in standard works of organic chemistry such as, for example, Houben-Weyl, Methoden der organischen Chemie, Thieme-Verlag, Stuttgart.

The polymerizable mesogenic compounds of formula III can be mono- or direactive, i.e. they can carry one or two polymerizable functional groups.

In a preferred embodiment of the invention the liquid crystalline materials comprise at least one inventive chiral dopant, at least one monoreactive and at least one direactive compound of formula III.

In another preferred embodiment the liquid crystalline materials comprise at least one inventive chiral dopant and at least two monoreactive compounds of formula III.

Preferably the liquid crystalline materials comprising chiral dopants of formula I and polymerizable mesogenic compounds of the formula III additionally comprise a polymerization initiator that decomposes when exposed to actinic radiation, such as for example UV light, or when heated above a certain temperature.

Another object of the invention are polymer films with an oriented chiral liquid crystalline phase obtainable by (co) polymerizing a liquid crystalline material comprising at least one chiral dopant of formula I and at least one polymerizable mesogenic compound preferably selected of formula III.

To prepare polymer films with a chiral liquid crystalline phase with uniform orientation the inventive liquid crystalline materials, for example, are coated onto a substrate, aligned and polymerized in situ by exposing them to heat or actinic radiation. Alignment and curing are carried out in the liquid crystalline phase of the liquid crystalline materials.

Polymerization can be achieved for example by using UV light and a photoinitiator that decomposes under UV irradiation. The polymerization may also be started by an initiator that decomposes when heated above a certain temperature.

As a substrate for example a glass plate or a plastic film can be used. To achieve uniform alignment, the film for example can be sheared by means of a doctor blade, or shearing can be caused by putting the polymerizable material between two substrates. It is also possible to apply an electric or magnetic field to the coated mixture.

A detailed description of the in situ polymerization of polymerizable mesogenic compounds can be found in D. J. Broer et al., Makromolekulare Chemie 190, 2255 (1989).

The inventive liquid crystalline materials can additionally comprise one or more other suitable components, such as, for example, catalysts, sensitizers, stabilizers, co-reacting monomers or surface-active compounds.

It is also possible to add, for example, non mesogenic compounds with two or more polymerizable functional groups to increase crosslinking of the polymers. Typical examples for difunctional non mesogenic monomers are alkyldiacrylates or alkyldimethacrylates. Typical examples for non mesogenic monomers with more than two polymerizable groups are trimethylpropanetrimethacrylate or pentaerythritoltetraacrylate.

For the preparation of anisotropic polymer gels, the liquid crystalline materials can be polymerized in situ as described above, however, in this case alignment of the polymerizable material is not necessary.

From the foregoing description, one skilled in the art can easily ascertain the essential characteristics of this invention, and without departing from the spirit and scope thereof, can make various changes and modifications of the invention to adapt it to various usages and conditions.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

In the foregoing and in the following examples, unless otherwise indicated, all temperatures are set forth uncorrected in degrees Celsius and all parts and percentages are by weight. The following abbreviations are used to illustrate the liquid crystalline phase behaviour of the compounds:

K=crystalline; N=nematic; S=smectic; Ch=cholesteric; I=isotropic. The numbers between these symbols indicate the phase transition temperatures in degree Celsius.

EXAMPLE 1

The compound (1a) was prepared according to reaction scheme 1.

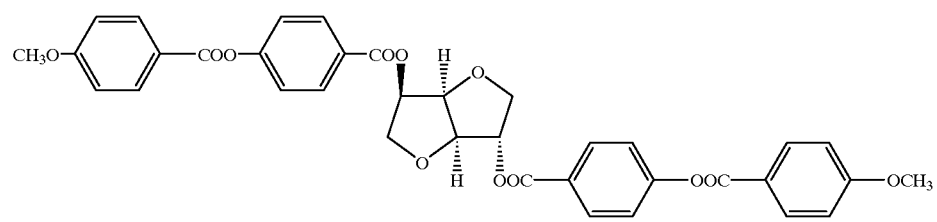

(1a)

The compound exhibits the phase behaviour K 139 I and shows a very high HTP of 75 $\mu m^{-1}$, determined in the commercially available nematic liquid crystal mixture E 063 (from Merck Ltd., Poole, UK) as a host mixture, which has the following properties

| | |
|---|---|
| clearing point | 78.5° C. |
| birefringence | 0.224 |
| dielectric anisotropy | +14.6 |
| viscosity (at 20° C.) | 38 mm²/s |

The following compounds have been prepared analogously

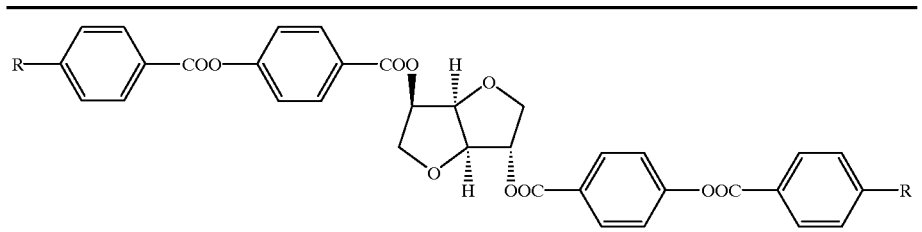

| No. | R | phase behaviour | HTP (in E 063) |
|---|---|---|---|
| 1b | $C_5H_{11}$ | K 126.1 I | 56 $\mu m^{-1}$ |
| 1c | $OC_6H_{13}$ | K 139.8 I | |
| 1d | $C_7H_{15}$ | K 133 I | |

EXAMPLE 2

The compound (2a) was prepared according to the reaction scheme 2. The compound has the phase behaviour K 221.9 I.

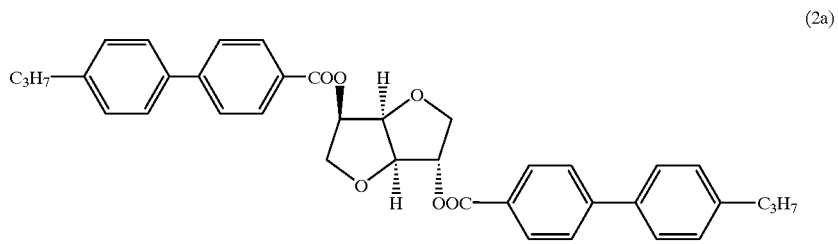

(2a)

The compound (2b) was prepared analoguously and exhibits the phase behaviour K 149.4 I.

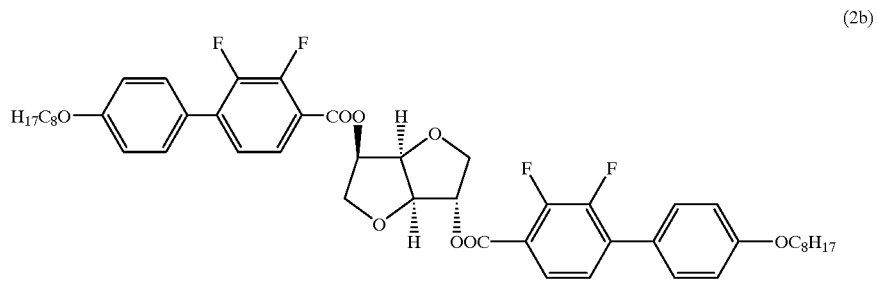

(2b)

EXAMPLE 3

The compound (3) was prepared according to reaction scheme 2. The compound has the phase behaviour K 171 I and shows a HTP of 36 $\mu m^{-1}$ measured in the host mixture E 063.

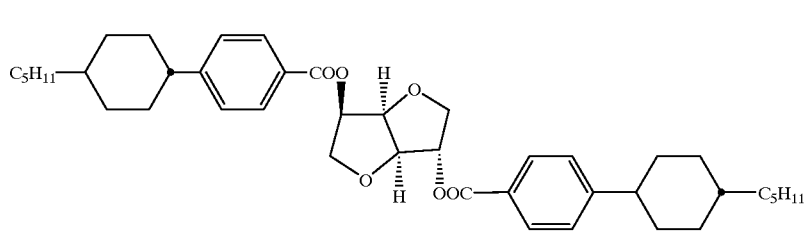
(3)

EXAMPLE 4

The compound (4) was prepared according to reaction scheme 2 and has the phase behaviour K 236 I.

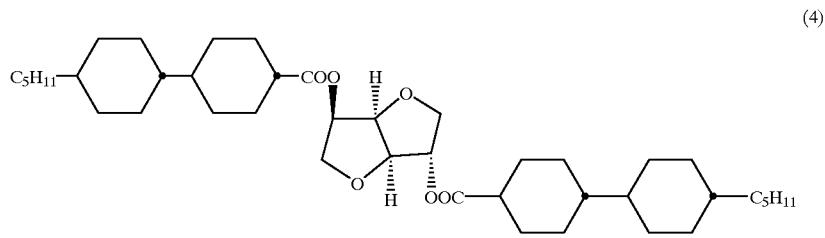
(4)

EXAMPLE 5

The compound (5) was prepared according to reaction scheme 1 and has the phase behaviour K 204 I.

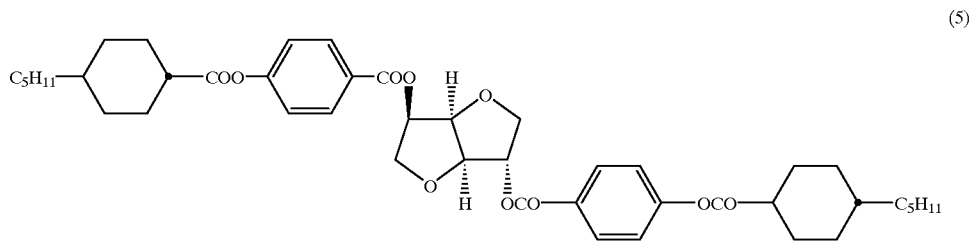
(5)

EXAMPLE 6

The following compounds were prepared according to reaction scheme 2.

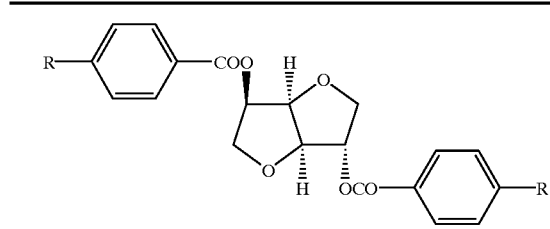

| No. | R | phase behaviour | HTP (in E 063) |
|---|---|---|---|
| 6a | OCH$_3$ | K 96.7 I | 51 μm$^{-1}$ |
| 6b | OC$_4$H$_9$ | K 102.3 I | |
| 6c | OC$_6$H$_{13}$ | K 89.4 I | |
| 6d | C$_5$H$_{11}$ | K 76.4 I | |

EXAMPLE 7

The compound (7) was prepared according to reaction scheme 2 and has the phase behaviour K 83.1 I.

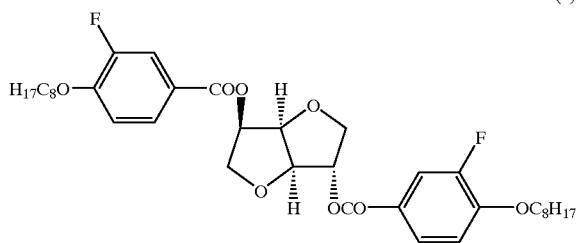

(7)

EXAMPLE 8

The compound (8) was prepared according to reaction scheme 2. The compound has the phase behaviour K 114 I and shows a HTP of 28 $\mu m^{-1}$ measured in the host mixture E 063.

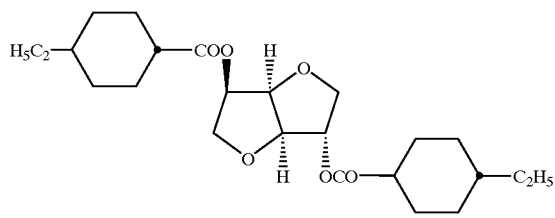

(8)

EXAMPLE 9

The following mixture was formulated

| compound (9) | 95.5% |
|---|---|
| compound (1a) | 3.5% |
| Irgacure 369 | 1.0% |

Irgacure 369 is a commercially available photoinitiator from Ciba Geigy AG (Basel, Switzerland).

Compound (9) is a direactive polymerizable compound which is disclosed e.g. in EP-A2-0 331 233.

The mixture has the phase behaviour Ch 118 I.

The mixture was cured as a thin film between two glass substrates using UV light with an irradiance of 3 mW/cm² at 80° C. to give a bright green cholesteric polymer film with a reflection wavelength maximum at 550 nm. The brightness of the film is significantly better than that of a film prepared by using a state of the art chiral dopant such as e.g. R-811 or CB 15 (commercially available from Merck KGaA, Darmstadt).

EXAMPLE 10

Compound (1a) was added at an amount of 3.5% by weight to the commercially available nematic liquid crystal mixture BL 106 (from Merck Ltd., Poole, UK) exhibiting the following properties:

| clearing point | 73.7° C. |
|---|---|
| birefringence | 0.213 |
| dielectric anisotropy | +16.6 |

After addition of the chiral dopant (1a), the mixture has the phase behaviour Ch 71 I, and shows a reflection wavelength λ of 572 nm. Thus the clearing point of BL 106 is only slightly altered by adding the dopant (1a).

EXAMPLE 11

Compound (6b) was added at an amount of 5.5% by weight to the commercially available nematic liquid crystal mixture E44 (from Merck Ltd, Poole, UK) exhibiting the following properties

| clearing point | 100° C. |
|---|---|
| birefringence | 0.263 |
| dielectric anisotropy | +16.8 |

After addition of the chiral dopant (6b), the mixture has the phase behaviour Ch 88.5 I, and shows a cholesteric reflection wavelength λ of 550 nm at 25° C. and 570 nm at 70° C., with a low temperature dependence dλ/dT of 0.44 nm/° C.

EXAMPLE 12

Compound (6b) was added at an amount of 5.0% by weight to the commercially available nematic liquid crystal mixture E63 (from Merck Ltd, Poole, UK) exhibiting the following properties

| clearing point | 88° C. |
|---|---|
| birefringence | 0.224 |
| dielectric anisotropy | +15.6 |

After addition of the chiral dopant (6b), the mixture has the phase behaviour Ch 77.4 I, and shows a cholesteric reflection wavelength λ of 583 nm at 25° C. and 604 nm at 70° C., with a low temperature dependence dλ/dT of 0.47 nm/° C.

EXAMPLE 13

Compound (6b) was added at an amount of 6.0% by weight to the commercially available nematic liquid crystal mixture MLC-6422 (from Merck Darmstadt, Germany) exhibiting the following properties

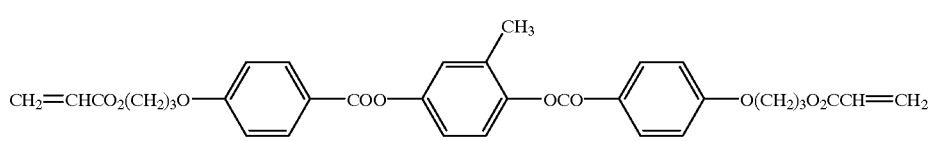

(9)

| | |
|---|---|
| clearing point | 93° C. |
| birefringence | 0.1978 |

After addition of the chiral dopant (6b), the mixture has the phase behaviour Ch 78.5 I, and shows a cholesteric reflection wavelength λ of 550 nm at 25° C. and 606 nm at 70° C., with a low temperature dependence dλ/dT of 1.24 nm/° C.

EXAMPLE 14

Compound (6d) was added at an amount of 7.0% by weight to the nematic liquid crystal mixture MLC-6422.

After addition of the chiral dopant (6d), the mixture has the phase behaviour Ch 72.9 I, and shows a cholesteric reflection wavelength λ of 558 nm at 25° C. and 644 nm at 70° C., with a low temperature dependence dλ/dT of 1.9 nm/° C.

EXAMPLE 15

Compound (6b) (7.0% by weight) and compound (6d) (4.0% by weight) were added to the nematic liquid crystal mixture MLC-6422.

After addition of the chiral dopants, the mixture shows a cholesteric reflection wavelength λ of 582 nm at 25° C. and 668 nm at 70° C., with a low temperature dependence dλ/dT of 1.9 nm/° C.

EXAMPLE 16

Compound (6c) was added at an amount of 4.5% by weight to the commercially available nematic liquid crystal mixture BL080 (from Merck Ltd, Poole, UK) exhibiting the following properties

| | |
|---|---|
| clearing point | 87.2° C. |
| birefringence | 0.1546 |
| dielectric anisotropy | +14.5 |

After addition of the chiral dopant (6c), the mixture shows a cholesteric reflection wavelength λ of 630 nm at 25° C. and 670 nm at 70° C., with a low temperature dependence dλ/dT of 0.80 nm/° C.

EXAMPLE 17

Compound (1a) was added at an amount of 4.5% by weight to the commercially available nematic liquid crystal mixture BL080. After addition of the chiral dopant (1a), the mixture has the phase behaviour Ch 83 I, showing only a slight reduction of the clearing point, and shows a cholesteric reflection wavelength λ of 520 nm at 25° C. and 508 nm at 70° C., with a low temperature dependence dλ/dT of −0.24 nm/° C.

The preceding examples can be repeated with similar success by substituting the generically or specifically described reactants and/or operating conditions of this invention for those used in the preceding examples.

What is claimed is:

1. A chiral dopant of formula I:

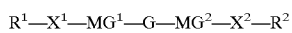

wherein

R$^1$ and R$^2$ are each independently a straight-chain or branched alkyl radical with up to 25 C atoms which may be unsubstituted, mono- or polysubstituted by halogen or CN, it being also possible for one or more non-adjacent CH$_2$ groups to be replaced, in each case independently from one another, by —O—, —S—, —NH—, —N(CH$_3$)—, —CO—, —COO—, —OCO—, —OCO—O—, —S—CO—, —C)—S— or —C≡C— in such a manner that oxygen atoms are not linked directly to one another, X$^1$ and X$^2$ are independently of each other —O—, —S—, —CO—, —COO—, —OCO—, —OCO—O—, —S—CO—, —CO—S— or a single bond, G is the following structure element MG$^1$ and MG$^2$ are each independently a mesogenic or mesogenity supporting group of the formula:

—(A$^1$—Z)$_m$—A$^2$— with

Z denoting —COO—, —OCO—, —CH$_2$CH$_2$—, —OCH$_2$—, —CH$_2$O—, —CH=CH—, —CH=CH—COO—, —OCO—CH=CH—, —C≡C— or a single bond, A$^1$ and A$^2$ being each independently 1,4-phenylene in which, in addition, one or more CH groups may be replaced by N, 1,4-cyclohexylene in which, in addition, one or two non-adjacent CH$_2$ groups may be replaced by O and/or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydronaphthalene-2,6-diyl, it being possible for all these groups to be unsubstituted, mono- or polysubstituted with halogen, cyano or nitro groups or alkyl, alkoxy or alkanoyl groups having 1 to 7 C atoms wherein one or more H atoms may be substituted by F or l, and m being 0, 1, 2 or 3 with the proviso that both MG$^1$ and MG$^2$ are not simultaneously 1,4-phenylene.

2. Chiral dopants according to claim 1, wherein MG$^1$ and MG$^2$ are selected from the following formulae

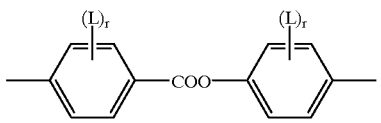

II a

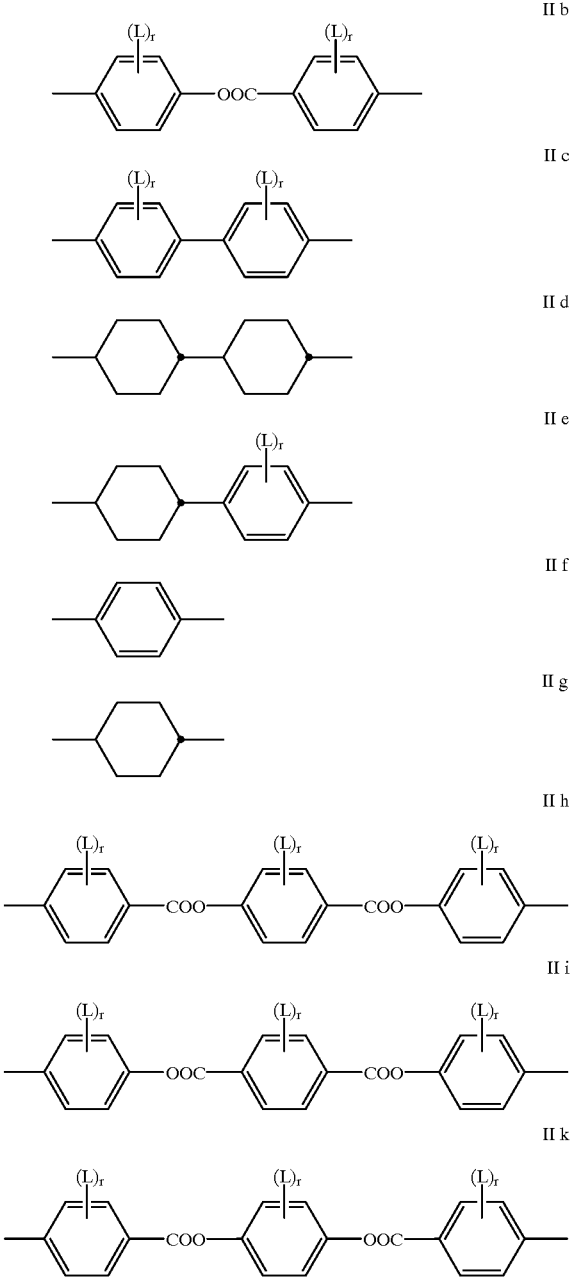

wherein L in each case independently denotes halogen, a cyano or nitro group or an alkyl, alkoxy or alkanoyl group having 1 to 7 C atoms wherein one or more H atoms may be substituted by F or Cl and r is 0, 1 or 2.

3. Chiral dopants according to claim 2, wherein r is 0 and $R^1$ and $R^2$ are each independently alkyl or alkoxy with 1 to 10 C atoms.

4. A liquid crystalline material comprising at least one chiral dopant according to claim 1.

5. A liquid crystalline material comprising at least one chiral dopant according to claim 1 and at least one polymerizable mesogenic compound having at least one polymerizable functional group.

6. A liquid crystalline material comprising 0.001 to 15% of weight of at least one chiral dopant according to claim 1.

7. A liquid crystalline material comprising a liquid crystalline material according to claim 4.

8. A polymer film with a chiral liquid crystalline phase comprising at least one chiral dopant according to claim 1.

9. A polymer film with a chiral liquid crystalline phase made by a process comprising coating a liquid crystalline material according to claim 5 onto a substrate.

10. A method of preparing a polymer film with a chiral liquid crystalline phase for an optical element, a color filter, or a display comprising coating a liquid crystal material according to claim 4 onto a substrate.

11. A liquid crystalline material according to claim 4, further comprising a low molecular weight nematic or nematogenic liquid crystalline compound.

12. A liquid crystalline material according to claim 11, wherein the low molecular weight nematic or nematogenic liquid crystalline compound is selected from azoxybenzenes, benzylideneanilines, biphenyls, terphenyls, phenyl or cyclohexyl benzoates, phenyl or cyclohexyl esters of cyclohehexanecarboxylic acid, phenyl or cyclohexyl esters or cyclohexylbenzoic acid, phenyl or cyclohexyl esters of cyclohexylcyclohexanecarboxylic acid, and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexylpyridazines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, halogenated stilbenes, benzyl phenyl ether, tolanes, or substituted cinnamic acids.

13. A liquid crystalline material according to claim 4, further comprising at least one compound of the formula

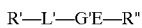

wherein L' and E, independently from one another, are a bivalent radical from the group formed by -Phe-, -Cyc-, -Phe-Phe-, -Phe-Cyc-, -Cyc-Cyc-, -Pyr-, -Dio-, -B-Phe- and -B-Cyc- and their mirror images, wherein Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and B is 2-(trans-1,4-cyclohexyl)ethyl, pyridimine-2,5-diyl, pyridine-2,5-diyl or 1,3-dioxane-2,5-diyl;

G' is selected from —CH=CH—, —N(O)N—, —CH=C—, —CH=N(O)—, —C≡C—, —CH$_2$—CH$_2$—, —CO—O—, —CH$_2$—O—, —CO—S—, —CH$_2$—S—, —CH=N, —COO—Phe—COO— or a single bond, with Y being halogen, or —CN;

R' and R" are, independently of one another, alkyl, alkenyl, alkoxy, alkenyloxy, alkanoyloxy, alkoxycarbonyl or alkoxycarbonyloxy with 1 to 18 atoms, or one of R' and R" is —F, —CR$_3$, —OCF$_3$, —Cl, —NCS or —CN.

14. A liquid crystalline material according to claim 5, further wherein the polymerizable mesogenic compound is of the formula P-(SP-X)$_n$-A-Z$^1$-B-(Z$^2$-C)$_p$- R$^3$ wherein
P is CH₂=CW—COO—, WCH=CH—O,

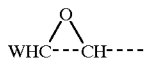

or CH₂=CH-Phenyl-(O)$_k$-with W being H, CH₃ or Cl and k being 0 or 1;
Sp is a spacer group having 1 to 20 C atoms;

X is a group selected from —O—, —S—, —CO—, —COO—, —OCO—, —OCO—O—, —S—CO—, —CO—S— or a single bond;
n is 0 to 1;
Z¹ and Z² are each independently —COO—, —OCO—, —CH₂CH₂—, —OCH₂—, —CH₂O—, —CH=CH, —CH≡CH—C—, —CH=CH—COO—, —OCO—CH=CH— or a single bond; wherein
A, B and C are each independently 1,4-phenylene in which, one or more CH groups may be replaced by N, 1,4-cyclohexylene in which, in addition, one or two non-adjacent CH₂ groups may be replaced by O and/or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydronaphthalene-2,6-diyl; optionally all these groups are unsubstituted, mono- or polysubstituted with halogen, cyano or nitro groups, or alkyl, alkoxy or alkanoyl groups having 1 to 7 C atoms wherein one or more H atoms may be substituted by F or Cl;
p is 0, 1 or 2; and
R³ is an alkyl radical with up to 25 C atoms which may be unsubstituted, mono- or polysubstituted by halogen or CN, optionally one or more non-adjacent CH₂ groups are replaced, independently from one another, by —O—, —S—, —NH—, —N(CH₃), —CO—, —COO— —OCO—, —OCO—O—, —S—CO—, —CO—S— or —C≡C— with the proviso that oxygen atoms are not linked directly to one another, or alternatively, R³ is halogen, cyano or is independent from P-(Sp-X)$_n$-.

15. A liquid crystalline material according to claim 5, wherein the polymerizable mesogenic compound is at least one of the following formulae:

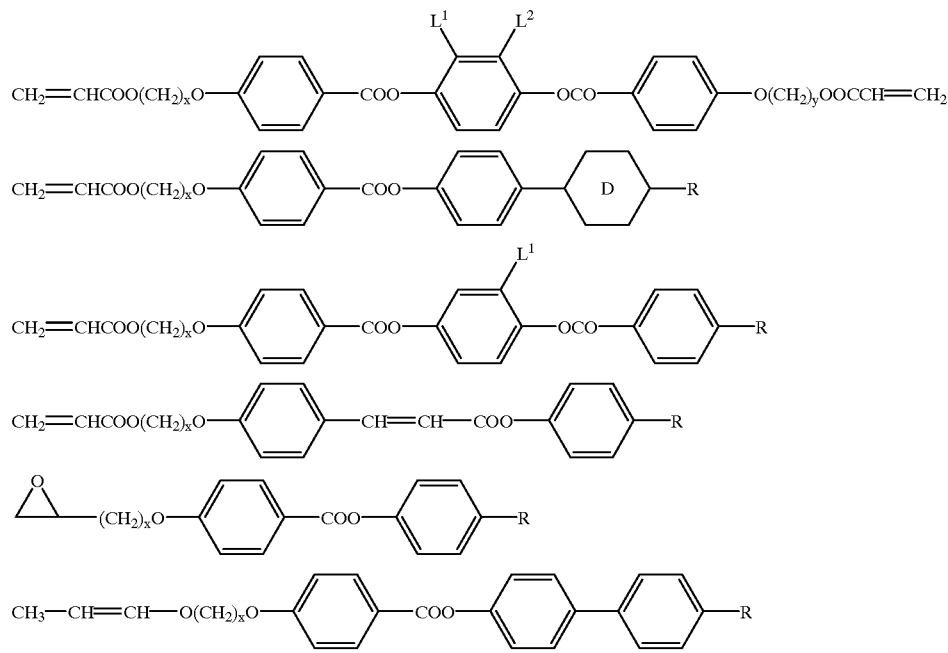

wherein x and y are each independently 1 to 12, D is a 1,4-phenylene or 1,4-cyclohexylene, R is selected from the group consisting of halogen, cyano and an alkyl or alkoxy with 1 to 12 C atoms, and L¹ and L² are each, independently, selected from the group consisting of H, halogen, CN, and an alkyl, alkoxy or alkanoyl with 1 to 7 C atoms.

16. A liquid crystalline material according to claim 4, further comprising at least one of a catalyst, a sensitizer, a stabilizer, a co-reacting monomer, or a surface-active compound.

17. A liquid crystal display, optical element, or color filter comprising a chiral dopant according to claim 1.

18. The display of claim 17, wherein the display is selected from the group consisting of a STN, TN, AMD-TN, temperature compensation, guest-host, phase change, polymer free cholesteric texture, and polymer stabilized cholesteric texture display.

19. A chiral dopant of formula I according to claim 1 wherein MG¹ and MG² are different.

20. A liquid crystalline material comprising at least one chiral dopant of formula I:

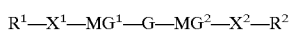

wherein
R¹ and R² are each independently a straight-chain or branched alkyl radical with up to 25 C atoms which may be unsubstituted, mono- or polysubstituted by halogen or CN, it being also possible for one or more non-adjacent $CH_2$ groups to be replaced, in each case independently from one another, by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another, $X^1$ and $X^2$ are independently of each other —O—, —S—, —CO—, —COO—, —OCO—, —OCO—O—, —S—CO—, —CO—S— or a single bond, G is the following structure element

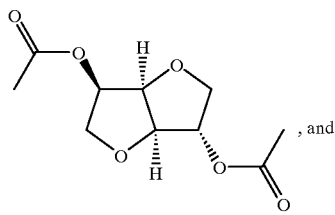, and $MG^1$ and $MG^2$ are each independently a mesogenic or mesogenity supporting group of the formula:

$-(A^1-Z)_m-A^2-$ with

Z denoting —COO—, —OCO—, —$CH_2CH_2$—, —$OCH_2$—, —$CH_2O$—, —CH=CH—, —CH=CH—COO—, —OCO—CH=CH—, —C≡C— or a single bond, $A^1$ and $A^2$ being each independently 1,4-phenylene in which, in addition, one or more CH groups may be replaced by N, 1,4-yclohexylene in which, in addition, one or two non-adjacent $CH_2$ groups may be replaced by O and/or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydronaphthalene-2,6-diyl, it being possible for all these groups to be unsubstituted, mono- or polysubstituted with halogen, cyano or nitro groups or alkyl, alkoxy or alkanoyl groups having 1 to 7 C atoms wherein one or more H atoms may be substituted by F or Cl, and m being 0, 1, 2 or 3 and at least one polymerizable mesogenic compound having at least one polymerizable functional group.

21. The liquid crystalline material according to claim 20, wherein $MG^1$ and $MG^2$ of the chiral dopant are selected from the following formulae II a
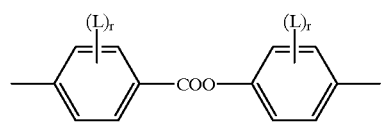

II b
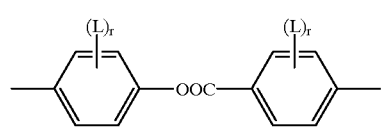

II c
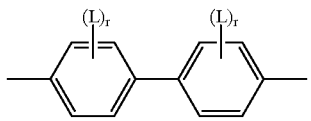

II d
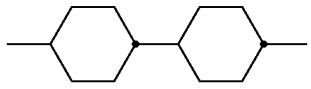

II e
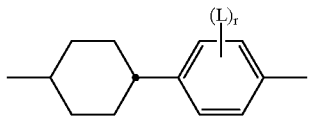

II f
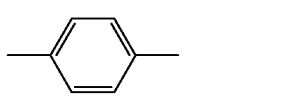

II g
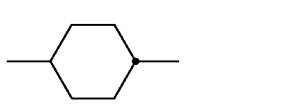

II h
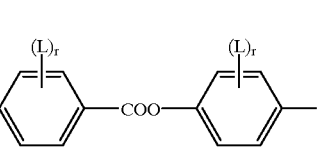

II i
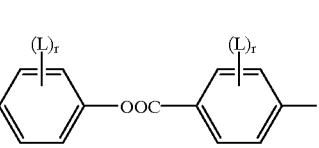

II k
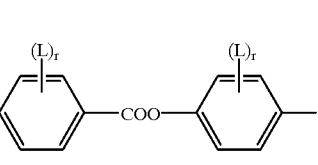

22. A liquid crystalline material according to claim 20, wherein the chiral dopant has r=0 and $R^1$ and $R^2$ are each independently alkyl or aloxy with 1–10 carbon atoms.

23. A liquid crystalline material according to claim 20, wherein $MG^1$ and $MG^2$ are different.

24. A polymer film with a chiral liquid crystalline phase comprising at least one chiral dopant of formula I $R^1-X^1-MG^1-G-MG^2-X^2-R^2$ wherein $R^1$ and $R^2$ are each independently a straight-chain or branched alkyl radical with up to 25 C atoms which may be unsubstituted, mono- or polysubstituted by halogen or CN, it being also possible for one or more non-adjacent $CH_2$ groups to be replaced, in each case independently form one another, by —O—, —S—, —NH—, —N($CH_3$)—, —CO—, —COO—, —OCO—, —OCO—O—, —S—CO—, —CO—S— or —C≡C— in such a manner that oxygen atoms are not linked directly to one another, $X^1$ and $X^2$ are independently of each other —O—, —S—, —CO—, —COO—, —OCO—, —OCO—O—, —S—CO—, —CO—S— or a single bond, G is the following structure element

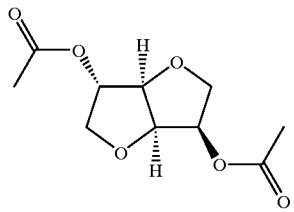

$MG^1$ and $MG^2$ are each independently a mesogenic or mesogenity supporting group of the formula

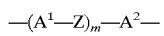

with

Z denoting —COO—, —OCO—, —CH$_2$CH$_2$—, —OCH$_2$—, —CH$_2$O—, —CH=CH—, —CH=CH—COO—, —OCO—CH=CH—, —C≡C— or a single bond, $A^1$ and $A^2$ being each independently 1,4-phenylene in which, in addition, one or more CH groups may be replaced by N, 1,4-cyclohexylene in which, in addition, one ore two non-adjacent CH$_2$ groups may be replaced by O and/or S, 1,4-cyclohexenylene, 1,4-bicyclo(2,2,2)octylene, piperidine-1,4-diyl, naphthalene-2,6-diyl, decahydronaphthalene-2,6-diyl, or 1,2,3,4-tetrahydronaphthalene-2,6-diyl, it being possible for all these groups to be unsubstituted, mono- or polysubstituted with halogen, cyano or nitro groups or alkyl, alkoxy or alkanoyl groups having 1 to 7 C atoms wherein one or more H atoms may be substituted by F or l, and m being 0, 1, 2 or 3.

* * * * *

UNITED STATES PATENT AND TRADEMARK OFFICE
CERTIFICATE OF CORRECTION

PATENT NO. : 6,217,792 B1
APPLICATION NO. : 09/214387
DATED : April 17, 2001
INVENTOR(S) : Owain Parri It is certified that error appears in the above-identified patent and that said Letters Patent is hereby corrected as shown below:

Column 24, line 56 reads "—CH=C—,—CH=N(O)—, —C≡C—, —CH$_2$—" should read -- —CH=CY—,—CH=N(O)—, —C≡C—, —CH$_2$— --
Column 24, line 63 reads "R' and R" is —F, —CR$_3$, —OCF$_3$, —Cl, —NCS or" should read --R' and R" is —F, —CF$_3$, —OCF$_3$, —Cl, —NCS or --
Column 25, line 46 reads "—CH≡CH—C—,—CH=CH—COO—, —OCO—" should read -- —CH≡CH, —C≡,—CH=CH—COO—, —OCO— --
Column 28, line 35 reads " 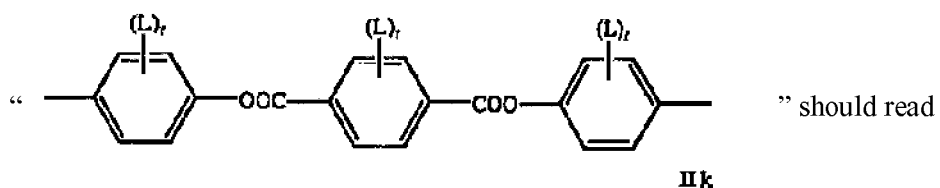 " should read -- 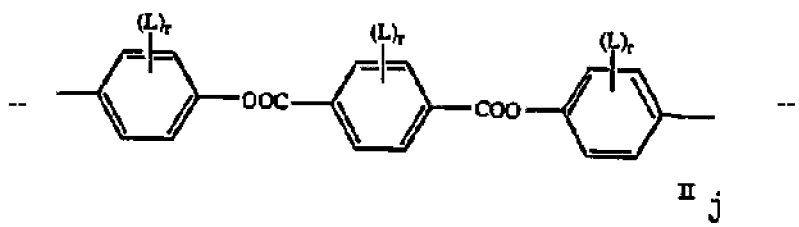 --

Signed and Sealed this

Eleventh Day of September, 2007

JON W. DUDAS
*Director of the United States Patent and Trademark Office*